(12) United States Patent
Hong et al.

(10) Patent No.: US 11,510,645 B2
(45) Date of Patent: Nov. 29, 2022

(54) ULTRASOUND IMAGING APPARATUS FOR PREDICTING FETAL GROWTH RATE AND METHOD OF OPERATING THE SAME

(71) Applicant: SAMSUNG MEDISON CO., LTD., Hongcheon-gun (KR)

(72) Inventors: Hoki Hong, Seongnam-si (KR); Daebong Park, Seongnam-si (KR); Sungnam Park, Seongnam-si (KR); Jaeho Lee, Seongnam-si (KR); Jeong Cho, Seongnam-si (KR); Soonjae Hong, Seongnam-si (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 307 days.

(21) Appl. No.: 16/366,024

(22) Filed: Mar. 27, 2019

(65) Prior Publication Data

US 2019/0298302 A1    Oct. 3, 2019

(30) Foreign Application Priority Data

Mar. 27, 2018    (KR) .................... 10-2018-0035396

(51) Int. Cl.
*A61B 8/08*    (2006.01)
*A61B 8/00*    (2006.01)
(Continued)

(52) U.S. Cl.
CPC .......... *A61B 8/0866* (2013.01); *A61B 8/4254* (2013.01); *A61B 8/4405* (2013.01);
(Continued)

(58) Field of Classification Search
CPC ......... A61B 5/107; A61B 8/0866; A61B 8/14; A61B 8/4254; A61B 8/4405;
(Continued)

(56) References Cited

U.S. PATENT DOCUMENTS 6,019,723 A    2/2000    Yamaura
8,012,091 B2    9/2011    Petraglia et al.
(Continued)

FOREIGN PATENT DOCUMENTS

EP    1932478 A1    6/2008
JP    2006-167162 A    6/2006
(Continued)

OTHER PUBLICATIONS

Communication dated Jul. 15, 2019, from the European Patent Office in counterpart European Application No. 19165143.9.
(Continued)

*Primary Examiner* — Yi-Shan Yang
*Assistant Examiner* — Alexei Bykhovski
(74) *Attorney, Agent, or Firm* — Sughrue Mion, PLLC (57) ABSTRACT

Provided is an ultrasound imaging apparatus for predicting fetal growth rate, including: an ultrasound probe configured to transmit ultrasound signals to a fetus and receive ultrasound echo signals reflected from the fetus; a user inputter configured to receive pregnancy information regarding a patient from a user; a communicator configured to receive, from a cloud server, fetal biometric data related to the pregnancy information regarding the patient from among fetal biometric data prestored and accumulated in the cloud server; and a controller configured to generate an ultrasound image of the fetus by using the ultrasound echo signals, measure a size of a body part of the fetus on the ultrasound image, and predict the fetal growth rate based on the measured size of the body part of the fetus and the fetal biometric data received from the cloud server.

10 Claims, 9 Drawing Sheets

(51) Int. Cl.
*A61B 5/107* (2006.01)
*A61B 8/14* (2006.01)

(52) U.S. Cl.
CPC .......... *A61B 8/4427* (2013.01); *A61B 8/4472* (2013.01); *A61B 8/461* (2013.01); *A61B 8/467* (2013.01); *A61B 8/5207* (2013.01); *A61B 8/5292* (2013.01); *A61B 8/565* (2013.01); *A61B 5/107* (2013.01); *A61B 8/14* (2013.01); *A61B 8/4411* (2013.01); *A61B 8/4477* (2013.01)

(58) Field of Classification Search
CPC ... A61B 8/4411; A61B 8/4427; A61B 8/4472; A61B 8/4477; A61B 8/461; A61B 8/467; A61B 8/5207; A61B 8/5292; A61B 8/565
See application file for complete search history.

(56) References Cited

U.S. PATENT DOCUMENTS

| | | |
|---|---|---|
| 2005/0096540 A1 | 5/2005 | Ooshima |
| 2006/0247527 A1 | 11/2006 | Maruyama |
| 2010/0222679 A1* | 9/2010 | Hall ..................... A61B 8/0858 600/443 |
| 2015/0035959 A1* | 2/2015 | Amble ................. A61B 5/0077 348/74 |
| 2015/0163219 A1 | 6/2015 | Lo et al. |
| 2017/0049414 A1 | 2/2017 | Venugopalan |

FOREIGN PATENT DOCUMENTS

| | | | |
|---|---|---|---|
| JP | 4068318 B2 | 3/2008 | |
| JP | 2008-099931 A | 5/2008 | |
| JP | 2010-187987 A | 9/2010 | |
| JP | 4599197 B2 | 12/2010 | |
| KR | 10-2014-0065710 A | 5/2014 | |
| KR | 101630071 * | 10/2014 | ............. A61B 5/107 |
| KR | 10-1630071 B1 | 6/2016 | |

OTHER PUBLICATIONS

Rebecca Simmons "Abnormalities of Fetal Growth" Avery's Diseases of the Newborn, Jan. 1, 2012, (pp. 51-59) XP055602788.

* cited by examiner

FIG. 7C

ULTRASOUND IMAGING APPARATUS FOR PREDICTING FETAL GROWTH RATE AND METHOD OF OPERATING THE SAME

CROSS-REFERENCE TO RELATED APPLICATION(S)

This application is based on and claims priority under 35 U.S.C. § 119 to Korean Patent Application No. 10-2018-0035396, filed on Mar. 27, 2018, in the Korean Intellectual Property Office, the disclosure of which is incorporated by reference herein in its entirety.

BACKGROUND

1. Field

The disclosure relates to ultrasound imaging apparatuses for predicting fetal growth rate by using an ultrasound image and methods of operating the ultrasound imaging apparatuses.

2. Description of Related Art

Recently, in the medical field, various types of medical imaging apparatuses have been widely used to visualize and acquire information about living tissue of a human body for early diagnosis or surgery with regard to various diseases. Representative examples of these medical imaging apparatuses may include an ultrasound imaging apparatus, a computed tomography (CT) apparatus, and a magnetic resonance imaging (MRI) apparatus.

Ultrasound imaging apparatuses transmit ultrasound signals generated by transducers of a probe to an object and receive information of echo signals reflected from the object, thereby obtaining an image of an internal part of the object. In particular, ultrasound imaging apparatuses are used for medical purposes including observing an internal area of an object, detecting foreign substances, and assessing injuries. Such ultrasound imaging apparatuses exhibit high stability, display images in real-time, and are safe due to lack of radiation exposure compared to diagnostic X-ray apparatuses. Therefore, ultrasound imaging apparatuses have been widely used together with other types of imaging diagnosis apparatuses.

One commonly used method involves transmitting ultrasound signals to a pregnant patient (a pregnant woman), measuring a size of a fetal body part on a fetal ultrasound image obtained using ultrasound echo signals reflected from the pregnant patient, and predicting fetal growth by comparing the measured size with a pregnant woman's gestational week. When predicting fetal growth based on a size of a fetal body part measured on an ultrasound image and a pregnant woman's gestational week, a gestational age (GA) table and a fetal growth table published in pre-compiled GA and fetal growth tables are applied to an ultrasound imaging apparatus and used as a reference. However, because results shown in the tables are applied to the ultrasound imaging apparatus, it is difficult to reflect updated data values related to fetal growth. Furthermore, the number of pieces of sample data used in the tables is limited, and a table is not sufficient to be used as a reference for the degree of fetal body development that differs according to geographical locations. Thus, a current method of predicting a fetal growth rate based on data from GA and fetal growth tables provides low prediction accuracy.

SUMMARY

Provided is an apparatus and method of predicting a fetal growth rate by using fetal biometric data received from a cloud server as reference data for information about a size of a fetal body part actually measured on an ultrasound image.

Additional aspects will be set forth in part in the description which follows and, in part, will be apparent from the description, or may be learned by practice of the presented embodiments of the disclosure.

According to an embodiment of the disclosure, a method of predicting a fetal growth rate by using an ultrasound imaging apparatus includes: receiving pregnancy information regarding a patient from a user of the ultrasound imaging apparatus; obtaining an ultrasound image of a fetus and measuring a size of a body part of the fetus on the obtained ultrasound image; receiving from a cloud server fetal biometric data related to the pregnancy information regarding the patient from among fetal biometric data prestored and accumulated in the cloud server; and predicting the fetal growth rate based on the measured size of the body part of the fetus and the received fetal biometric data.

The receiving of the fetal biometric data may include receiving from the cloud server big data related to the fetal biometric data with respect to a gestational week, which is obtained by a plurality of different ultrasound imaging apparatuses and stored in the cloud server.

The measuring of the size of the body part of the fetus may include measuring at least one of a biparietal diameter (BPD), an abdominal circumference (AC), a head circumference (HC), an occipitofrontal diameter (OFD), or a femur length (FL) of the fetus on the ultrasound image.

The receiving of the pregnancy information regarding the patient may include receiving information about a last menstrual period (LMP) of the patient or a date of conception (DOC) of the fetus.

The receiving of the fetal biometric data may include receiving the fetal biometric data related to characteristic information of the patient from among big data with respect to a fetal biometric value, which is stored in the cloud server, wherein the characteristic information includes at least one of a location, an age, or physical characteristics of the patient.

The predicting of the fetal growth rate may include updating a gestational age table and a fetal growth table by using the fetal biometric data received from the cloud server and predicting the fetal growth rate based on a result of the updating and the measured size of the body part of the fetus.

The method may further include: displaying a graph with a gestational week of the patient as a first axis and the fetal biometric data received from the cloud server as a second axis; and displaying on the graph a mark representing a value of a size of a body part of the fetus, wherein the size of the body part is measured with respect to the gestational week.

According to another embodiment of the disclosure, an ultrasound imaging apparatus for predicting fetal growth rate includes: an ultrasound probe configured to transmit ultrasound signals to the fetus and receive ultrasound echo signals reflected from the fetus; a user inputter configured to receive, from a user, pregnancy information regarding a patient; a communicator configured to receive from a cloud server fetal biometric data related to the pregnancy information regarding the patient from among fetal biometric data prestored and accumulated in the cloud server; and a controller configured to generate an ultrasound image of the fetus by using the ultrasound echo signals, measure a size of a body part of the fetus on the ultrasound image, and predict the fetal growth rate based on the measured size of the body part of the fetus and the fetal biometric data received from the cloud server.

The communicator may be further configured to receive from the cloud server big data related to fetal biometric data with respect to a gestational week, which is obtained by a plurality of different ultrasound imaging apparatuses and stored in the cloud server.

The controller may be further configured to measure at least one of a BPD, an AC, a HC, an OFD, or a FL of the fetus on the ultrasound image.

The user inputter may be further configured to receive information about a patient's LMP or DOC.

The controller may be further configured to control the communicator to receive the fetal biometric data related to characteristic information of the patient from among big data with respect to a fetal biometric value, which is stored in the cloud server, wherein the characteristic information includes at least one of a location, an age, or physical characteristics of the patient.

The controller may be further configured to update a gestational age table and a fetal growth table by using the fetal biometric data received from the cloud server and predict the fetal growth rate based on a result of the updating and the measured size of the body part of the fetus.

The ultrasound imaging apparatus may further include a display displaying a graph with a gestational week of the patient as a first axis and the fetal biometric data received from the cloud server as a second axis.

The display may display on the graph a mark representing a value of a size of a body part of the fetus, wherein the size of the body part is measured with respect to the gestational week.

According to another embodiment of the disclosure, a computer program product includes a computer-readable storage medium. The computer-readable storage medium includes instructions for: receiving pregnancy information regarding a patient from a user of an ultrasound imaging apparatus; obtaining an ultrasound image of a fetus and measuring a size of a body part of the fetus on the obtained ultrasound image; receiving from a cloud server fetal biometric data related to the pregnancy information regarding the patient from among fetal biometric data prestored and accumulated in the cloud server; and predicting the fetal growth rate based on the measured size of the body part of the fetus and the received fetal biometric data.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

The present specification describes principles of the present disclosure and sets forth embodiments thereof to clarify the scope of the present disclosure and to allow those of ordinary skill in the art to implement the embodiments of the disclosure. The present embodiments of the disclosure may have different forms and should not be construed as being limited to the descriptions set forth herein.

Like reference numerals refer to like elements throughout. The present specification does not describe all components in the embodiments of the disclosure, and common knowledge in the art or the same descriptions of the embodiments of the disclosure will be omitted below. The term "part" or "portion" used herein may be implemented using hardware or software, and according to embodiments of the disclosure, a plurality of "parts" or "portions" may be formed as a single unit or element, or one "part" or "portion" may include a plurality of units or elements.)

Hereinafter, the operating principles and embodiments of the disclosure will be described in detail with reference to the accompanying drawings.

In exemplary embodiments, an image may include any medical image acquired by various medical imaging apparatuses such as a magnetic resonance imaging (MRI) apparatus, a computed tomography (CT) apparatus, an ultrasound imaging apparatus, or an X-ray apparatus.

Also, in the present specification, an "object", which is a thing to be imaged, may include a human, an animal, or a part thereof. For example, an object may include a part of a human, that is, an organ or a tissue, or a phantom.

Throughout the specification, an ultrasound image refers to an image of an object processed based on ultrasound signals transmitted to the object and reflected therefrom.

Throughout the disclosure, the expression "at least one of a, b or c" indicates only a, only b, only c, both a and b, both a and c, both b and c, all of a, b, and c, or variations thereof.

Figure 1:
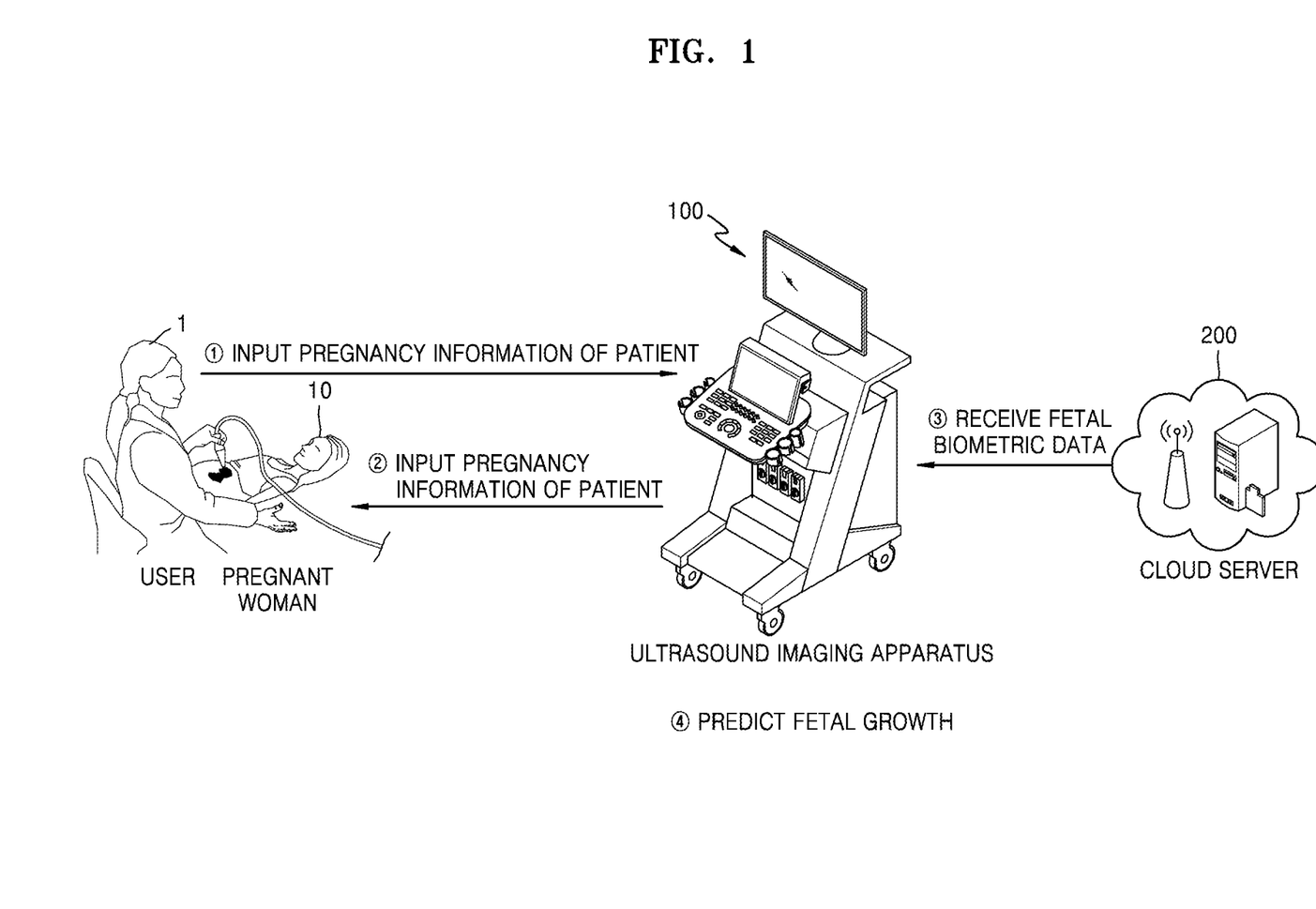
FIG. 1 is a conceptual diagram for explaining a method whereby an ultrasound imaging apparatus predicts fetal growth rate from an ultrasound image, according to an embodiment of the disclosure.

FIG. 1 is a conceptual diagram for explaining a method whereby an ultrasound imaging apparatus 100 predicts a fetal growth rate from an ultrasound image of a fetus, according to an embodiment of the disclosure.

Referring to FIG. 1, the ultrasound imaging apparatus 100 receives pregnancy information regarding a patient from a user 1. In this case, the patient may be a pregnant woman 10 carrying a fetus in her womb. The pregnancy information regarding the patient, which is received from the user 1 by the ultrasound imaging apparatus 100, may include at least one of a last menstrual period (LMP) or a date of conception (DOC).

The ultrasound imaging apparatus 100 transmits ultrasound signals to an abdomen of the pregnant woman 10 via an ultrasound probe and obtains an ultrasound image of a fetus by receiving ultrasound echo signals reflected from the pregnant woman 10. The ultrasound imaging apparatus 100 also measures a size of a fetal body part on the ultrasound image of the fetus. According to an embodiment of the disclosure, the ultrasound imaging apparatus 100 may measure a size of a fetal body part, including at least one of biparietal diameter (BPD), abdominal circumference (AC), head circumference (HC), occipitofrontal diameter (OFD), or femur length (FL) of the fetus in the ultrasound image.

The ultrasound imaging apparatus 100 receives from a cloud server 200, fetal biometric data related to the pregnancy information regarding the pregnant woman 10 from among pieces of fetal biometric data stored in the cloud server 200. The ultrasound imaging apparatus 100 may transmit information about a size of a fetal body part measured on the ultrasound image to the cloud server 200. The cloud server 200 may collect pieces of information about a size of a fetal body part from a plurality of different ultrasound imaging apparatuses to store big data with respect to a fetal biometric value. According to an embodiment of the disclosure, the ultrasound imaging apparatus 100 may receive from the cloud server 200 fetal biometric data related to the pregnancy information regarding the pregnant woman 10 from among big data with respect to a fetal biometric value, which have been prestored and accumulated in the cloud server 200.

The ultrasound imaging apparatus 100 predicts a fetal growth rate based on a size of a fetal body part measured on the ultrasound image and fetal biometric data received from the cloud server 200. According to an embodiment of the disclosure, the ultrasound imaging apparatus 100 may update a gestational age (GA) table and a fetal growth table to newer ones by using fetal metric data received from the cloud server 200 as a reference and predict a fetal growth rate based on the resulting updated GA and fetal growth tables and an actually measured size of a fetal body part.

According to a method of the related art, a GA table and a fetal growth table published in pre-compiled GA and fetal growth tables are applied to the ultrasound imaging apparatus 100, and a fetal growth rate is predicted by using the GA table and the fetal growth table as reference data for a fetal body size measured on an actually captured ultrasound image. However, because results shown in the tables are applied to the ultrasound imaging apparatus 100, it is difficult to reflect latest data values when predicting the fetal growth rate. In other words, it is inconvenient to update software of the ultrasound imaging apparatus 100 with latest published tables in order to reflect latest information about fetal biometric data. Furthermore, the number of pieces of sample data used in the tables is limited, and a table is not sufficient to be used as a reference for the degree of fetal body development that may differ according to geographical locations.

According to an embodiment of the disclosure, the ultrasound imaging apparatus 100 may receive from the cloud server 200 fetal biometric data related to pregnancy information regarding the patient, i.e., the pregnant woman 10, from among big data with respect to a fetal biometric value and predict a fetal growth rate by using the received fetal biometric data as a reference for a size of a fetal body part measured on the ultrasound image, thereby improving prediction accuracy.

Figure 2:
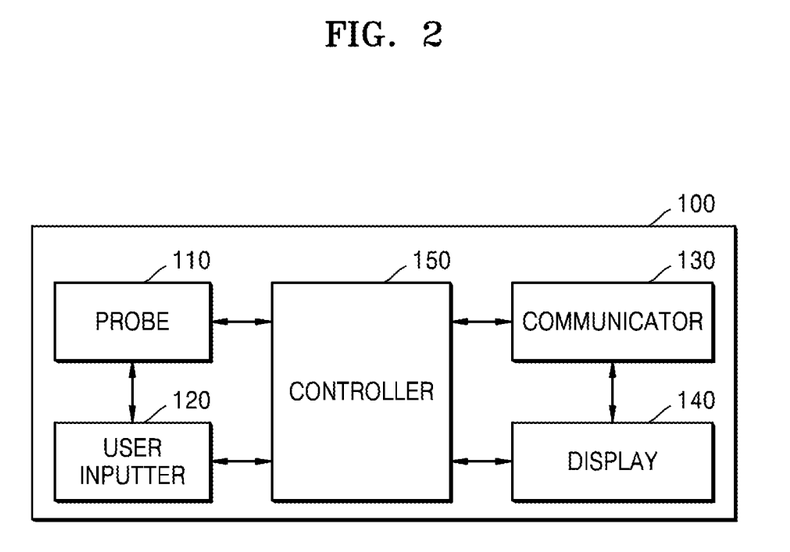
FIG. 2 is a block diagram of a configuration of an ultrasound imaging apparatus according to an embodiment of the disclosure.

FIG. 2 is a block diagram of a configuration of an ultrasound imaging apparatus 100 according to an embodiment of the disclosure.

Referring to FIG. 2, the ultrasound imaging apparatus 100 may include a probe 110, a user inputter 120, a communicator 130, a display 140, and a controller 150. The ultrasound imaging apparatus 100 may be implemented as a cart type apparatus as well as a portable type apparatus. Examples of portable ultrasound imaging apparatuses may include, but are not limited to, a picture archiving and communication system (PACS) viewer, a hand-carried cardiac ultrasound (HCU) device, a smartphone, a laptop computer, a personal digital assistant (PDA), and a tablet PC.

The probe 110 may include a plurality of transducers. The transducers may transmit ultrasound signals to an object, i.e., a patient. The transducers may also receive ultrasound echo signals reflected from the object to generate reception signals. Furthermore, the probe 110 may be integrally with the ultrasound imaging apparatus 100, or the probe 110 may be separate from the ultrasound imaging apparatus 100 but be connected thereto via a wire or wirelessly. In addition, the ultrasound imaging apparatus 100 may include one or more probes 110 according to its implemented configuration.

The user inputter 120 may receive a user input for controlling the ultrasound imaging apparatus 100. The user inputter 120 may receive pregnancy information of a patient from a user. According to an embodiment of the disclosure, the user inputter 120 may receive information about a LMP or DOC of a patient, i.e., a pregnant woman.

The user input received by the user inputter 120 may include an input for manipulating a button, a keypad, a mouse, a trackball, a jog switch, or a knob, an input for touching a touchpad or a touch screen, a voice input, a motion input, and a bioinformation input (e.g., iris recognition, fingerprint recognition, etc.), but is not limited thereto.

The communicator 130 may include one or more components that enable communication with an external device. For example, the communicator 130 may include at least one of a local area communication module, a wired communication module, or wireless communication module. For example, the communicator 130 may exchange a control signal and data with an external apparatus by using at least one of wireless communication methods including a Wireless Local Area Network (WLAN), Wireless Fidelity (Wi-Fi), Bluetooth, Zigbee, Wi-Fi Direct (WFD), Infrared Data Association (IrDA), Bluetooth Low Energy (BLE), Near Field Communication (NFC), Wireless Broadband Internet (WiBro), World Interoperability for Microwave Access (WiMAX), Shared Wireless Access Protocol (SWAP), Wireless Gigabit Alliance (WiGig), and radio frequency (RF) communication.

The communicator 130 may receive fetal biometric data prestored in a cloud server. The cloud server may store big data related to pieces of fetal biometric data with respect to a gestational week, which are obtained by a plurality of different ultrasound imaging apparatuses. The communicator 130 may receive from the cloud server fetal biometric data related to pregnancy information of the patient from among big data with respect to a fetal biometric value, which are stored in the cloud server.

According to an embodiment of the disclosure, the communicator 130 may transmit to the cloud server a data value obtained by measuring a body part of a pregnant patient's fetus, which is acquired by the controller 150.

The display 140 may display a fetal biometric data value with respect to a patient's gestational week in a graph form. According to an embodiment of the disclosure, the display 140 may display a graph with a patient's gestational week as a first axis (an X-axis) and a fetal biometric data value received from the cloud server as a second axis (an Y-axis).

According to an embodiment of the disclosure, the display 140 may display on the graph a mark indicating a size of a fetal body part measured with respect to a gestational week, as will be described in more detail with reference to FIG. 5.

For example, the display 140 may be constructed by a physical device including at least one of a cathode ray tube (CRT) display, a liquid crystal display (LCD), a plasma display panel (PDP), an organic light-emitting display (OLED), a field emission display (FED), a light-emitting diode (LED) display, a vacuum fluorescent display (VFD), a digital light processing (DLP) display, a flat panel display (FPD), a three-dimensional (3D) display, or a transparent display, but is not limited thereto. According to an embodiment of the disclosure, the display 140 may be formed as a touch screen including a touch interface. When the display 140 is formed as a touch screen, the display 140 may be integrated with a touch pad to receive a user touch input.

The controller 150 may control operations of the probe 110, the user inputter 120, the communicator 130, and the display 140. The controller 150 may generate an ultrasound image of a fetus by using ultrasound echo signals received via the probe 110 and measure a size of a fetal body part on the ultrasound image. According to an embodiment of the disclosure, the controller 150 may measure a size of a fetal body part, including at least one of BPD, AC, HC, OFD, or FL of the fetus on the ultrasound image. The controller 160 may measure a size of a fetal body part on the ultrasound image displayed according to a freeze input received via the user inputter 120. The controller 150 may measure the size of the fetal body part on the ultrasound image by using an image processing technique known in the art, and thus, a detail description thereof will be omitted here.

The controller 150 may predict a fetal growth rate based on the size of the fetal body part measured on the ultrasound image and fetal biometric data received from the cloud server. According to an embodiment of the disclosure, the controller 150 may control the communicator 130 to receive fetal biometric data related to characteristic information of a patient from among big data with respect to a fetal biometric value, which are stored in the cloud server. The characteristic information may include at least one of a patient's location, age, or physical characteristics.

According to an embodiment of the disclosure, the controller 150 may update a GA table and a fetal growth table to new ones by using fetal biometric data received from the cloud server and predict a fetal growth rate based on the resulting updated GA table and fetal growth table and a measured size of a fetal body part.

For example, the controller 150 may be composed of a hardware module including at least one of a central processing unit (CPU), a microprocessor, a graphics processing unit, random access memory (RAM), or read-only memory (ROM).

According to an embodiment of the disclosure, the controller 150 may also be implemented as an application processor (AP). According to another embodiment of the disclosure, the controller 150 may be implemented as a hardware component such as a field-programmable gate array (FPGA) or an application-specific integrated circuit (ASIC). However, embodiments of the disclosure are not limited thereto, and the controller 150 may include components such as software components, object-oriented software components, class components and task components, processes, functions, attributes, procedures, subroutines, segments of program code, drivers, firmware, micro codes, circuits, data, a database, data structures, tables, arrays, or variables.

Figure 3:
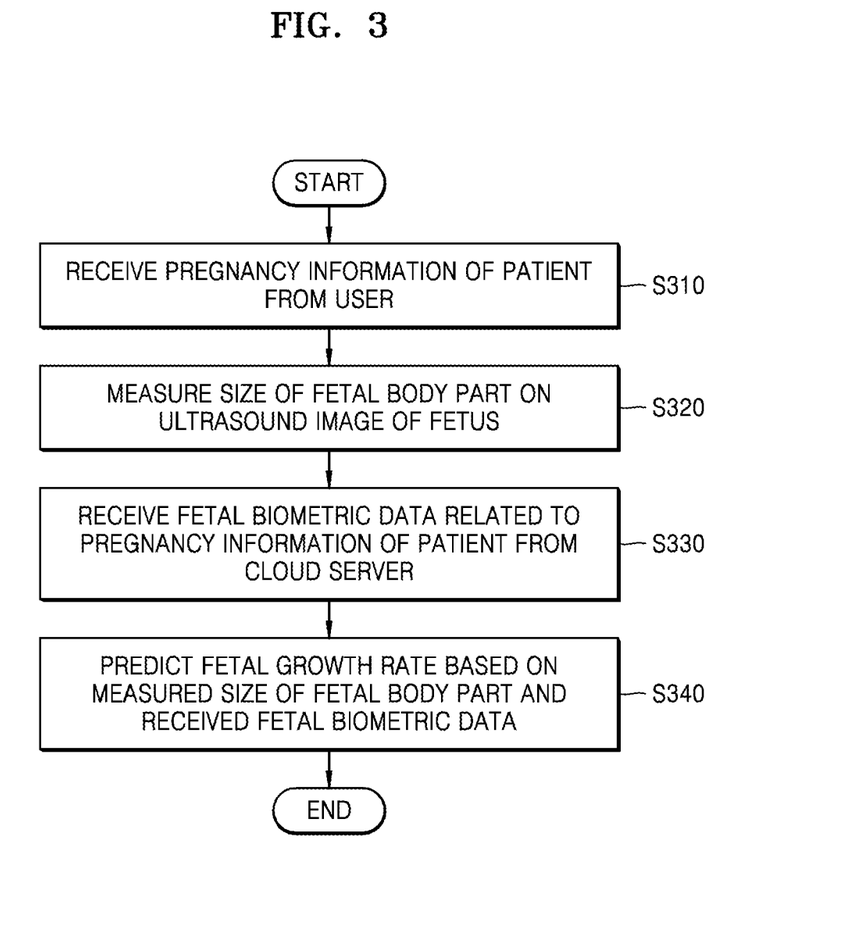
FIG. 3 is a flowchart of a method, performed by an ultrasound imaging apparatus, of predicting fetal growth rate from an ultrasound image, according to an embodiment of the disclosure.

FIG. 3 is a flowchart of a method, performed by an ultrasound imaging apparatus, of predicting a fetal growth rate from an ultrasound image, according to an embodiment of the disclosure.

The ultrasound imaging apparatus receives pregnancy information regarding a patient (a pregnant woman) from a user (S310). According to an embodiment of the disclosure, the ultrasound imaging apparatus may receive information about a patient's LMP or DOC from the user.

The ultrasound imaging apparatus measures a size of a fetal body part on an ultrasound image of a fetus (S320). The ultrasound imaging apparatus may transmit ultrasound signals to the patient and receive ultrasound echo signals reflected from the patient via a probe to thereby obtain an ultrasound image.

After obtaining the ultrasound image, the ultrasound imaging apparatus may freeze the ultrasound image displayed on a display according to a user input and measure a size of a fetal body part on the ultrasound image, For example, the ultrasound imaging apparatus may measure a size of a fetal body part, including at least one of BPD, AC, HC, OFD, or FL of the fetus on the ultrasound image.

The ultrasound imaging apparatus receives fetal biometric data related to the pregnancy information regarding the patient from a cloud server (S330). The cloud server may receive pieces of fetal biometric data obtained by a plurality of different ultrasound imaging apparatuses to store the received pieces of fetal biometric data in the form of big data. According to an embodiment of the disclosure, the ultrasound imaging apparatus may receive from the cloud server fetal biometric data related to the pregnancy information regarding the patient, which are received in operation S310, from among big data with respect to a fetal biometric value stored in the cloud server.

The ultrasound imaging apparatus predicts a fetal growth rate based on the measured size of the fetal body part and the fetal biometric data received from the cloud server (S340). The ultrasound imaging apparatus may receive from the cloud server the fetal biometric data related to the pregnancy information regarding the patient from among big data with respect to a fetal biometric value stored in the cloud server and predict a fetal growth rate by using the received fetal biometric data as reference data for the size of the fetal body part measured on the ultrasound image. According to an embodiment of the disclosure, the ultrasound imaging apparatus may update a GA table and a fetal growth table to newer ones by using the fetal biometric data received from the cloud server and predict a fetal growth rate based on the resulting updated GA and fetal growth tables and the measured size of the fetal body part.

Figure 4:
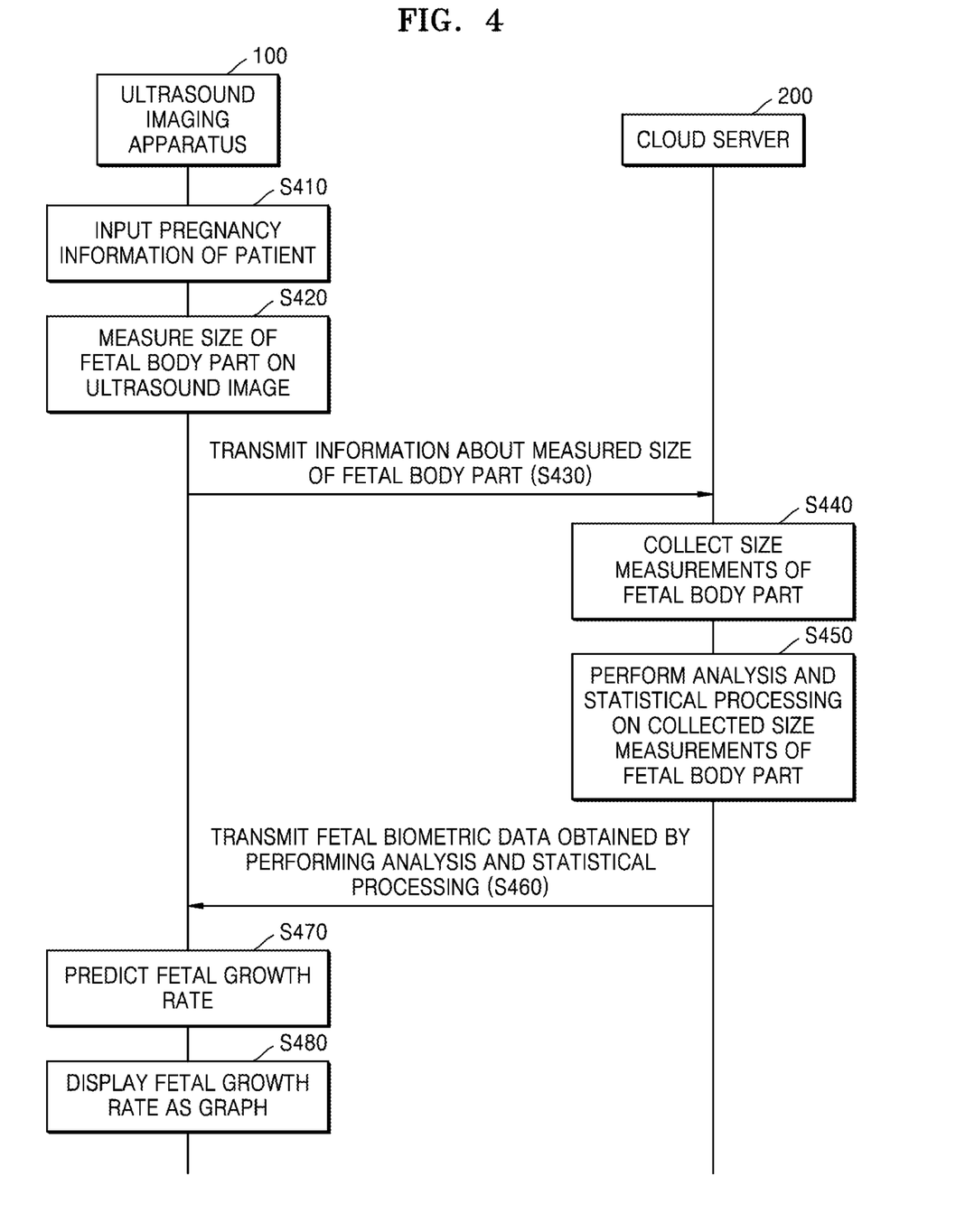
FIG. 4 is a flowchart of a method, performed by an ultrasound imaging apparatus, of predicting fetal growth rate by receiving fetal biometric data from a cloud server, according to an embodiment of the disclosure.

FIG. 4 is a flowchart of a method, performed by an ultrasound imaging apparatus 100, of predicting a fetal growth rate by receiving fetal biometric data from a cloud server 200, according to an embodiment of the disclosure.

The ultrasound imaging apparatus 100 receives pregnancy information of a patient (S410). According to an embodiment of the disclosure, the ultrasound imaging apparatus 100 may receive information about a patient's LMP or DOC from a user.

The ultrasound imaging apparatus 100 measures a size of a fetal body part on an ultrasound image (S420). The ultrasound imaging apparatus 100 may obtain an ultrasound image of a fetus being carried by the patient and measure a size of a fetal body part on the ultrasound image by using an image processing technique. According to an embodiment of the disclosure, the ultrasound imaging apparatus 100 may measure a size of a fetal body part, including at least one of measure a size of a fetal body part, including at least one of BPD, AC, HC, OFD, or FL of the fetus on the ultrasound image.

The ultrasound imaging apparatus 100 transmits information about the measured size of the fetal body part to the cloud server 200 (S430). According to an embodiment of the disclosure, the ultrasound imaging apparatus 100 may transmit the size of the fetal body part measured in operation S420 to the cloud server 200, together with the pregnancy information of the patient received in operation S410. For example, the ultrasound imaging apparatus 100 may transmit information about a gestational week calculated based on a time point when the ultrasound image is obtained to the cloud server 200, together with the size of the fetal body part.

The cloud server 200 collects size measurements of the fetal body part (S440). According to an embodiment of the disclosure, the cloud server 200 may receive pieces of fetal body part size data obtained by a plurality of different ultrasound imaging apparatuses including the ultrasound imaging apparatus 100 for storage.

The cloud server 200 performs analysis and statistical processing on the collected size measurements of the fetal body part (S450). According to an embodiment of the disclosure, the cloud server 200 may classify size measurements of a fetal body part, which are collected from a plurality of different ultrasound imaging apparatuses, into a plurality of categories according to at least one of a location, an age, or physical characteristics of a patient (a pregnant woman). The cloud server 200 may perform statistical processing on the size measurements of the fetal body part classified into the categories and store a result of the statistical processing as big data.

The cloud server 200 transmits fetal biometric data obtained by performing the analysis and statistical processing to the ultrasound imaging apparatus 100 (S460). According to an embodiment of the disclosure, the ultrasound imaging apparatus 100 may transmit to the cloud server 200 a signal requesting transmission of fetal biometric data related to the pregnancy information of the patient received in operation S410. The cloud server 200 may transmit, based on the received requesting signal, fetal biometric data related to the pregnancy information of the patient from among prestored big data to the ultrasound imaging apparatus 100. The fetal biometric data means fetal biometric data related to and obtained as a result of classification based on at least one of a patient's location, age, or physical characteristics.

The ultrasound imaging apparatus 100 predicts a fetal growth rate based on the pregnancy information of the patient received in operation S410, the size of the fetal body part measured in operation S420, and the fetal biometric data received in operation S460 (S470). According to an embodiment of the disclosure, the ultrasound imaging apparatus 100 may update a GA table and a fetal growth table to newer ones by using the fetal biometric data received from the cloud server 200 and predict a fetal growth rate based on the resulting updated GA and fetal growth tables and the measured size of the fetal body part.

The ultrasound imaging apparatus 100 displays the fetal growth rate as a graph (S480). An embodiment of the disclosure in which the ultrasound imaging apparatus 100 predicts a fetal growth rate via a display will now be described in more detail with reference to FIG. 5.

Figure 5:
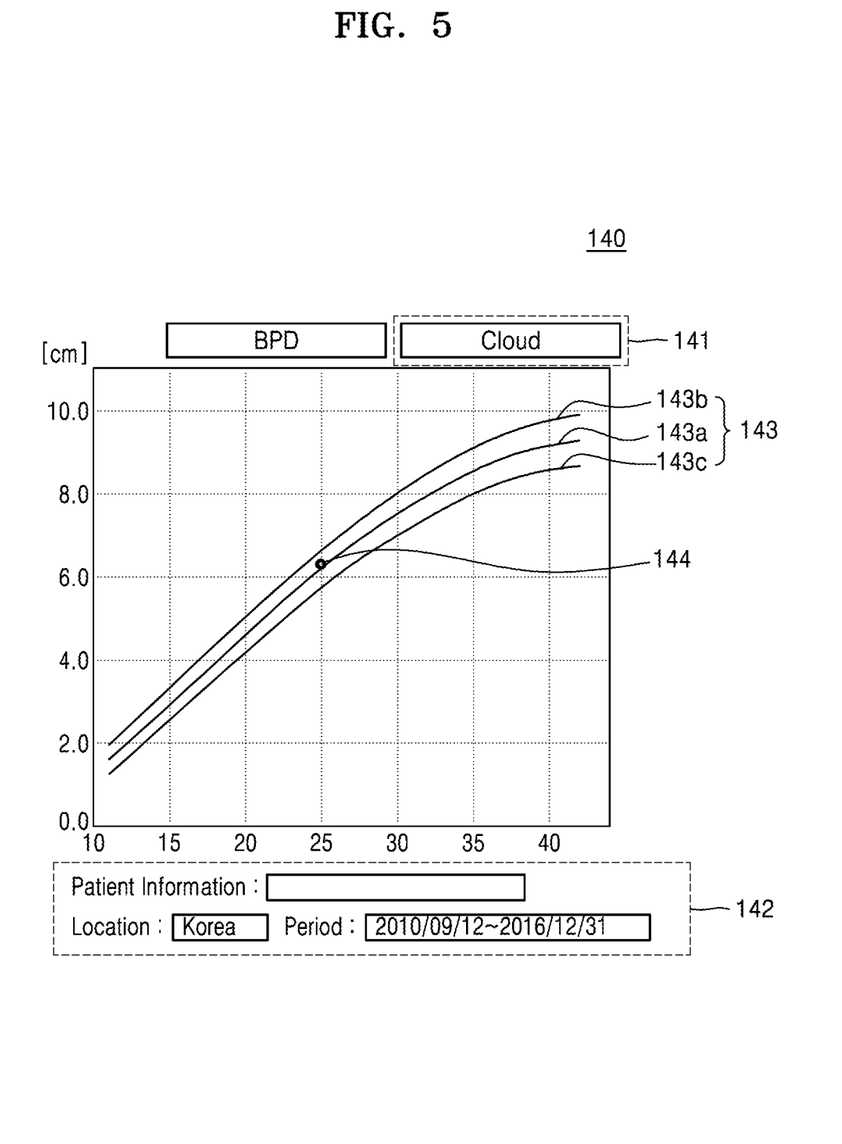
FIG. 5 illustrates an example of an operation of an ultrasound imaging apparatus displaying a graph of fetal growth rate, according to an embodiment of the disclosure.

FIG. 5 illustrates an example of an operation of an ultrasound imaging apparatus displaying a graph of a fetal growth rate on a display 140, according to an embodiment of the disclosure.

Referring to FIG. 5, the display 140 may display a first user interface (UI) 141 indicating fetal biometric data received from a cloud server, a second UI 142 indicating pregnancy information of a patient, a graph 143 showing fetal biometric data, and a mark 144 indicating an actually measured size of a fetal body part.

The first UI 141 may be a UI indicating that data values displayed on the graph 143 mean big data with respect to a fetal biometric value received from the cloud server (200 of FIG. 1).

The second UI 142 may be a UI indicating the pregnancy information of the patient. The second UI 142 may display identification information of the patient (the pregnant woman), such as a patient's name, age, address, nationality, etc., and information about a gestational week. The gestational week may be calculated based on a patient's LMP. The gestational week may be calculated by subtracting the LMP from a date when an ultrasound image is captured, or may be received directly from a user when an estimated date of delivery is determined during a previous check-up.

The graph 143 may be a graph obtained by plotting a gestational week on a first axis (an X-axis) and fetal biometric data values received from the cloud server 200 along a second axis (a Y-axis). A fetal biometric data value on the second axis (the Y-axis) may be expressed in centimeters (cm), but is not limited thereto. Fetal biometric data values displayed on the second axis (the Y-axis) are data values of one of fetal BPD, AC, HC, OFD, and FL received from the cloud server 200, and the data values may be plotted against a gestational week. In the embodiment of the disclosure shown in FIG. 5, the graph 143 may show measurement data of fetal BPD.

The graph 143 may include a total of three graphs, i.e., first through third graphs 143a through 143c. The first graph 143a may be obtained by plotting a statistical average value of fetal biometric data against a gestational week. According to an embodiment of the disclosure, the first graph 143a may be obtained by statically processing measurement values of a fetal body part, which are collected by the cloud server 200. The second and third graphs 143b and 143c may each indicate a difference corresponding to a statistical deviation with respect to the first graph 143a. The second and third graphs 143b and 143c may be respectively obtained by shifting the first graph 143a up (in a positive (+) direction) and down (in a negative (−) direction) by a predetermined deviation.

The mark 144 may be a UI displaying a size of a fetal body part actually measured on an ultrasound image with respect to a gestational week. In the embodiment of the disclosure shown in FIG. 5, the mark 144 displayed on the display 140 may indicate a size of a fetal body part measured on an ultrasound image captured at the time when a pregnant woman is 25 weeks pregnant. As seen on FIG. 5, a value indicated by the mark 144 is greater than a data value at week 25 of gestation on the first graph 143a, and thus, a fetus being carried by the pregnant woman may be predicted to grow faster than average.

In the embodiment shown in FIG. 5, by displaying a graph of fetal biometric data received from the cloud server 200 together with a size of a fetal body part measured on an actually captured ultrasound image, the ultrasound imaging apparatus may easily predict a fetal growth rate and accordingly provide improved user convenience.

Figure 6:
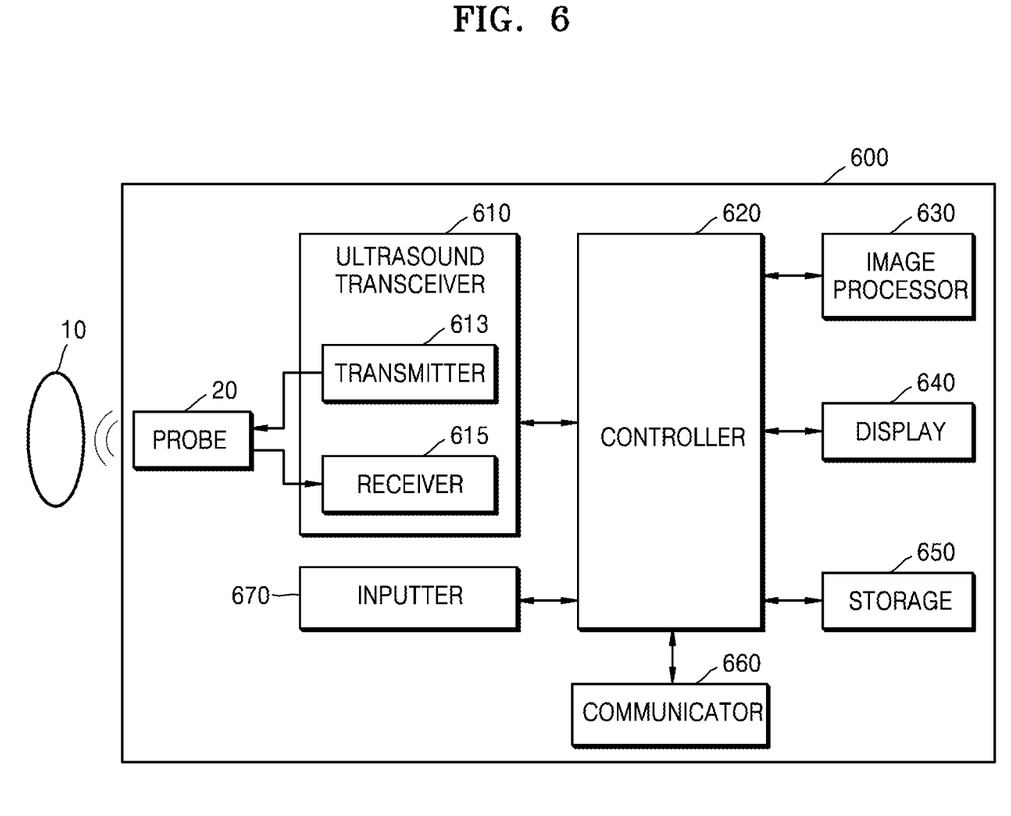
FIG. 6 is a block diagram of a configuration of an ultrasound imaging apparatus according to an embodiment of the disclosure.

FIG. 6 is a block diagram illustrating a configuration of an ultrasound imaging apparatus 600, i.e., a diagnostic apparatus, according to an exemplary embodiment.

Referring to FIG. 6, the ultrasound imaging apparatus 600 may include a probe 20, an ultrasound transceiver 610, a controller 620, an image processor 630, one or more displays 640, a storage 650, e.g., a memory, a communicator 660, i.e., a communication device or an interface, and an inputter 670.

The ultrasound imaging apparatus 600 may be of a cart-type or a portable-type ultrasound imaging apparatus that is portable, moveable, mobile, or hand-held. Examples of the portable-type ultrasound imaging apparatus may include a smart phone, a laptop computer, a personal digital assistant (PDA), and a tablet personal computer (PC), each of which may include a probe and a software application, but embodiments of the disclosure are not limited thereto.

The probe 20 may include a plurality of transducers. The plurality of transducers may transmit ultrasound signals to an object 10 in response to transmitting signals received by the probe 20, from a transmitter 613. The plurality of transducers may receive ultrasound signals reflected from the object 10 to generate reception signals. In addition, the probe 20 and the ultrasound imaging apparatus 600 may be formed in one body (e.g., disposed in a single housing), or the probe 20 and the ultrasound imaging apparatus 600 may be formed separately (e.g., disposed separately in separate housings) but linked wirelessly or via wires. In addition, the ultrasound imaging apparatus 600 may include one or more probes 20 according to embodiments of the disclosure.

The controller 620 may control the transmitter 613 to generate transmitting signals to be applied to each of the plurality of transducers based on a position and a focal point of the plurality of transducers included in the probe 20.

The controller 620 may control a receiver 615 to generate ultrasound data by converting reception signals received from the probe 20 from analogue to digital signals and summing the reception signals converted into digital form, based on a position and a focal point of the plurality of transducers.

The image processor 630 may generate an ultrasound image by using ultrasound data generated from the receiver 615.

The display 640 may display a generated ultrasound image and various pieces of information processed by the ultrasound imaging apparatus 600. The ultrasound imaging apparatus 600 may include two or more displays 640 according to the present exemplary embodiment. The display 640 may include a touch screen in combination with a touch panel.

The controller 620 may control the operations of the ultrasound imaging apparatus 600 and flow of signals between the internal elements of the ultrasound imaging apparatus 600. The controller 620 may include a memory for storing a program or data to perform functions of the ultrasound imaging apparatus 600 and a processor and/or a microprocessor (not shown) for processing the program or data. For example, the controller 620 may control the operation of the ultrasound imaging apparatus 600 by receiving a control signal from the inputter 670 or an external apparatus.

The ultrasound imaging apparatus 600 may include the communicator 660 and may be connected to external apparatuses, for example, servers, medical apparatuses, and portable devices such as smart phones, tablet personal computers (PCs), wearable devices, etc., via the communicator 660.

The communicator 660 may include at least one element capable of communicating with the external apparatuses. For example, the communicator 660 may include at least one among a short-range communication module, a wired communication module, and a wireless communication module.

The communicator 660 may receive a control signal and data from an external apparatus and transmit the received control signal to the controller 620 so that the controller 620 may control the ultrasound imaging apparatus 600 in response to the received control signal.

The controller 620 may transmit a control signal to the external apparatus via the communicator 660 so that the external apparatus may be controlled in response to the control signal of the controller 620.

For example, the external apparatus connected to the ultrasound imaging apparatus 600 may process the data of the external apparatus in response to the control signal of the controller 620 received via the communicator 660.

A program for controlling the ultrasound imaging apparatus 600 may be installed in the external apparatus. The program may include command languages to perform part of operation of the controller 620 or the entire operation of the controller 620.

The program may be pre-installed in the external apparatus or may be installed by a user of the external apparatus by downloading the program from a server that provides applications. The server that provides applications may include a recording medium where the program is stored.

The storage 650 may store various data or programs for driving and controlling the ultrasound imaging apparatus 600, input and/or output ultrasound data, ultrasound images, applications, etc.

The inputter 670 may receive a user's input to control the ultrasound imaging apparatus 600 and may include a keyboard, button, keypad, mouse, trackball, jog switch, knob, a touchpad, a touch screen, a microphone, a motion input means, a biometrics input means, etc. For example, the user's input may include inputs for manipulating buttons, keypads, mice, trackballs, jog switches, or knobs, inputs for touching a touchpad or a touch screen, a voice input, a motion input, and a bioinformation input, for example, iris recognition or fingerprint recognition, but an embodiment of the disclosure is not limited thereto.

An example of the ultrasound imaging apparatus 600 according to the embodiment of the disclosure is described below with reference to FIGS. 7A, 7B, and 7C.

Figure 7A:
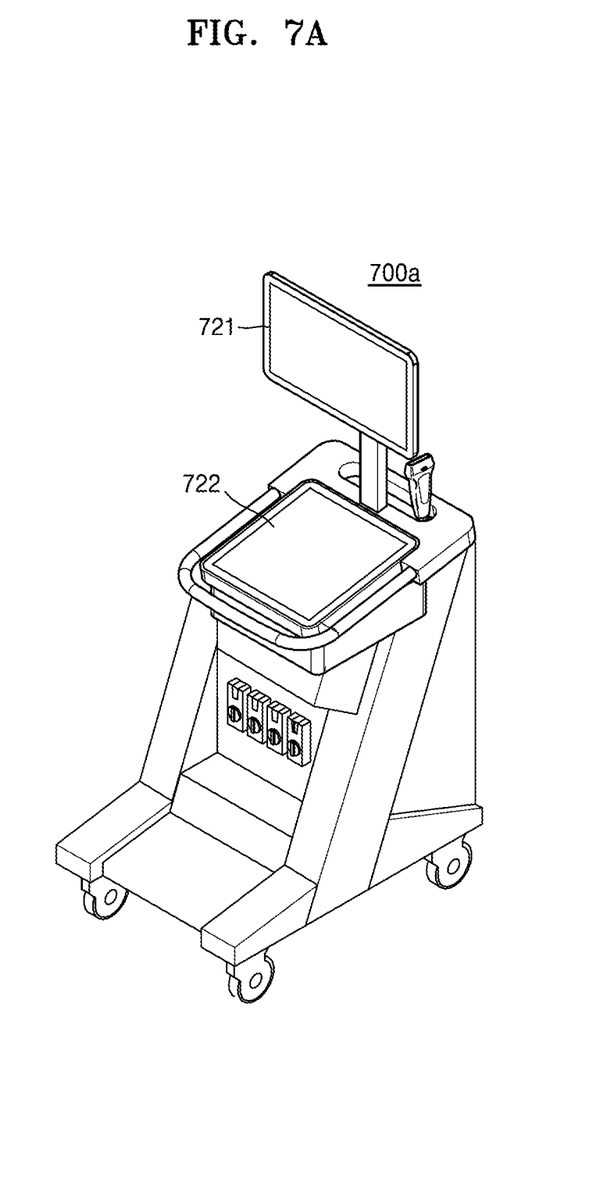
FIGS. 7A through 7C illustrate ultrasound imaging apparatuses according to embodiments of the disclosure.
Figure 7B:
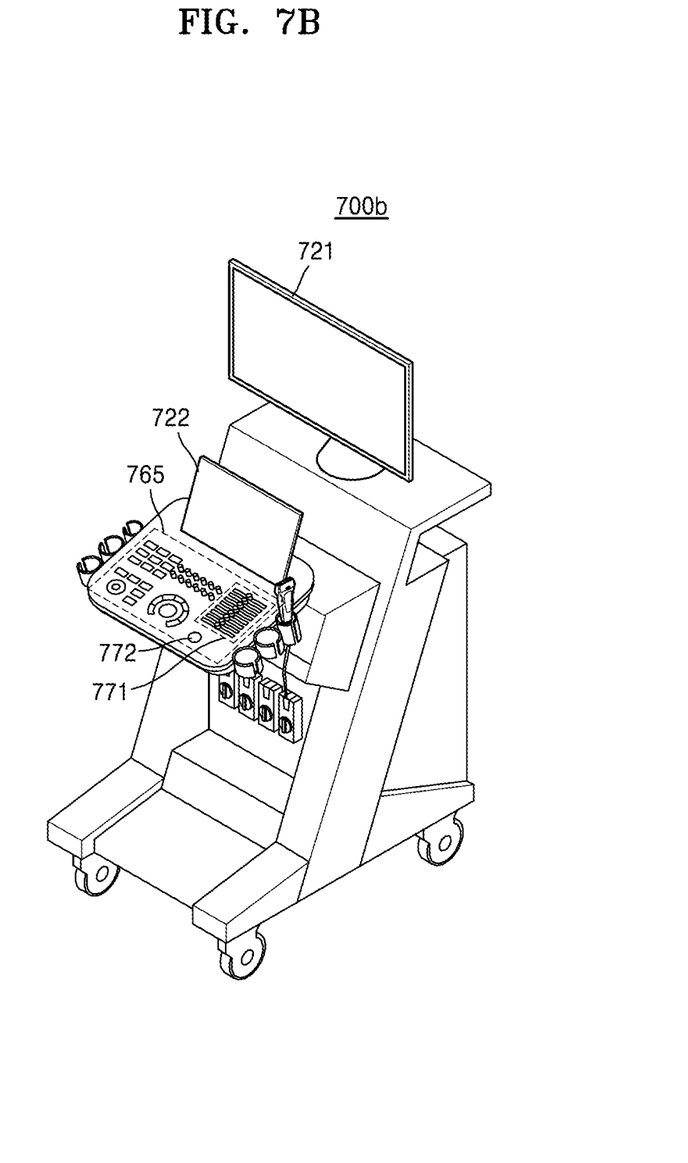
Figure 7C:
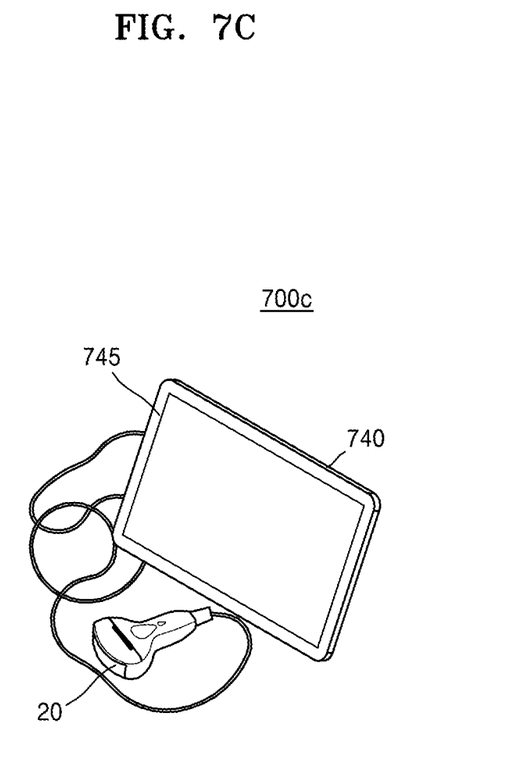

FIGS. 7A, 7B, and 7C are diagrams illustrating ultrasound imaging apparatus according to an exemplary embodiment.

Referring to FIGS. 7A and 7B, the ultrasound imaging apparatuses 700a and 700b may include a main display 721 and a sub-display 722. At least one among the main display 721 and the sub-display 722 may include a touch screen. The main display 721 and the sub-display 722 may display ultrasound images and/or various information processed by the ultrasound imaging apparatuses 700a and 700b. The main display 721 and the sub-display 722 may provide graphical UIs (GUIs), thereby receiving user's inputs of data to control the ultrasound imaging apparatuses 700a and 700b. For example, the main display 721 may display an ultrasound image and the sub-display 722 may display a control panel to control display of the ultrasound image as a GUI. The sub-display 722 may receive an input of data to control the display of an image through the control panel displayed as a GUI. The ultrasound imaging apparatuses 700a and 700b may control the display of the ultrasound image on the main display 721 by using the input control data.

Referring to FIG. 7B, the ultrasound imaging apparatus 700b may include a control panel 765. The control panel 765 may include buttons, trackballs, jog switches, or knobs, and may receive data to control the ultrasound imaging apparatus 1000b from the user. For example, the control panel 765 may include a time gain compensation (TGC) button 771 and a freeze button 772. The TGC button 771 is to set a TGC value for each depth of an ultrasound image. Also, when an input of the freeze button 772 is detected during capturing of an ultrasound image, the ultrasound imaging apparatus 700b may keep displaying a frame image at that time point.

The buttons, trackballs, jog switches, and knobs included in the control panel 765 may be provided as a GUI to the main display 721 or the sub-display 722.

Referring to FIG. 7C, the ultrasound imaging apparatus 700c may include a portable device. An example of the portable ultrasound imaging apparatus may include, for example, smart phones including probes and applications, laptop computers, personal digital assistants (PDAs), or tablet PCs, but an exemplary embodiment of the disclosure is not limited thereto.

The ultrasound imaging apparatus 700c may include the probe 20 and a main body 1400. The probe 20 may be connected to one side of the main body 740 by wire or wirelessly. The main body 740 may include a touch screen 745. The touch screen 745 may display an ultrasound image, various pieces of information processed by the ultrasound imaging apparatus 700c, and a GUI.

According to embodiments of the disclosure, latest fetal biometric data may be acquired by updating fetal biometric data stored and accumulated in a cloud server, and the acquired fetal biometric data may be used as a reference for a size of a fetal body part measured on a real ultrasound image. Thus, accuracy of prediction of fetal growth may be improved.

The embodiments of the disclosure may be implemented as a software program including instructions stored in a computer-readable storage medium.

A computer may refer to a device configured to retrieve an instruction stored in the computer-readable storage medium and to operate, in response to the retrieved instruction, and may include ultrasound imaging apparatuses 100, 600, 700a, 700b, and 700c according to embodiments of the disclosure.

The computer-readable storage medium may be provided in the form of a non-transitory storage medium. In this regard, the term 'non-transitory' means that the storage medium does not include a signal and is tangible, and the term does not distinguish between data that is semi-permanently stored and data that is temporarily stored in the storage medium.

In addition, the ultrasound imaging apparatus 100, 600, 700a, 700b, or 700c or the method of controlling the ultrasound imaging apparatus according to embodiments of the disclosure may be provided in the form of a computer program product. The computer program product may be traded, as a product, between a seller and a buyer.

The computer program product may include a software program and a computer-readable storage medium having stored thereon the software program. For example, the computer program product may include a product (e.g. a downloadable application) in the form of a software program electronically distributed by a manufacturer of the ultrasound imaging apparatus or through an electronic market (e.g., Google™, Play Store™, and App Store™). For such electronic distribution, at least a part of the software program may be stored on the storage medium or may be temporarily generated. In this case, the storage medium may be a storage medium of a server of the manufacturer, a server of the electronic market, or a relay server for temporarily storing the software program.

In a system consisting of a server and a terminal (e.g., the ultrasound imaging apparatus), the computer program product may include a storage medium of the server or a storage medium of the terminal. Alternatively, in a case where a third device (e.g., a smartphone) that communicates with the server or the terminal is present, the computer program product may include a storage medium of the third device. Alternatively, the computer program product may include a software program that is transmitted from the server to the terminal or the third device or that is transmitted from the third device to the terminal.

In this case, one of the server, the terminal, and the third device may execute the computer program product, thereby performing the method according to embodiments of the disclosure. Alternatively, at least two of the server, the terminal, and the third device may execute the computer program product, thereby performing the method according to embodiments of the disclosure in a distributed manner.

For example, the server (e.g., a cloud server, an artificial intelligence (AI) server, or the like) may execute the computer program product stored in the server, and may control the terminal to perform the method according to embodiments of the disclosure, the terminal communicating with the server.

As another example, the third device may execute the computer program product, and may control the terminal to perform the method according to embodiments of the disclosure, the terminal communicating with the third device. In more detail, the third device may remotely control the ultrasound imaging apparatus to emit X-ray to an object, and to generate an image of an inner part of the object, based on detected radiation which passes the object and is detected in an X-ray detector.

As another example, the third device may execute the computer program product, and may directly perform the method according to embodiments of the disclosure, based on at least one value input from an auxiliary device (e.g., a gantry of CT system). In more detail, the auxiliary device may emit X-ray to an object and may obtain information of radiation which passes the object and is detected in an X-ray detector. The third device may receive an input of signal information about the detected radiation from the auxiliary device, and may generate an image of an inner part of the object, based on the input radiation information.

In a case where the third device executes the computer program product, the third device may download the computer program product from the server, and may execute the downloaded computer program product. Alternatively, the third device may execute the computer program product that is pre-loaded therein, and may perform the method according to the embodiments of the disclosure.

While embodiments of the disclosure have been particularly shown and described with reference to the accompanying drawings, it will be understood by those of ordinary skill in the art that various changes in form and details may be made therein without departing from the spirit and scope of the disclosure as defined by the appended claims. The disclosed embodiments should be considered in descriptive sense only and not for purposes of limitation.

What is claimed is:

1. A method of predicting fetal growth rate by using an ultrasound imaging apparatus, the method comprising:
receiving pregnancy information regarding a patient from a user of the ultrasound imaging apparatus;
obtaining an ultrasound image of a fetus and measuring a size of a body part of the fetus on the obtained ultrasound image;

transmitting, to a cloud server prestoring and accumulating fetal biometric data, a request signal requesting transmission of the fetal biometric data related to the received pregnancy information regarding the patient;
receiving, from the cloud server, the fetal biometric data;
predicting the fetal growth rate based on the measured size of the body part of the fetus and the fetal biometric data received from the cloud server;
displaying a graph with a gestational week of the patient as a first axis and the fetal biometric data received from the cloud server as a second axis; and
displaying a first user interface including a text indicating that the fetal biometric data is received from the cloud server and a second user interface indicating the pregnancy information,
wherein the receiving of the fetal biometric data comprises:
receiving a first data included in the fetal biometric data, the first data being related to the pregnancy information regarding the patient, and
receiving a second data included in the fetal biometric data, the second data being related to characteristic information of the patient from among first big data with respect to a fetal biometric value,
wherein the characteristic information is stored in the cloud server,
wherein the characteristic information comprises at least one of a location, an age, or physical characteristics of the patient,
wherein the graph, the first user interface, and the second user interface are displayed at the same time in different areas of a display,
wherein the receiving of the fetal biometric data comprises receiving, from the cloud server, second big data related to the fetal biometric data with respect to the gestational week, and
wherein the fetal biometric data is obtained by a plurality of different ultrasound imaging apparatuses and stored in the cloud server.

2. The method of claim 1, wherein the measuring of the size of the body part of the fetus comprises measuring at least one of a biparietal diameter (BPD), an abdominal circumference (AC), a head circumference (HC), an occipitofrontal diameter (OFD), or a femur length (FL) of the fetus on the ultrasound image.

3. The method of claim 1, wherein the receiving of the pregnancy information regarding the patient comprises receiving information about a last menstrual period (LMP) of the patient or a date of conception (DOC) of the fetus.

4. The method of claim 1, wherein the predicting of the fetal growth rate comprises:
updating a gestational age table and a fetal growth table by using the fetal biometric data received from the cloud server; and
predicting the fetal growth rate based on a result of the updating and the measured size of the body part of the fetus.

5. The method of claim 1, further comprising:
displaying on the graph a mark representing a value of the size of the body part of the fetus, wherein the size of the body part is measured with respect to the gestational week.

6. An ultrasound imaging apparatus for predicting fetal growth rate, the ultrasound imaging apparatus comprising:
an ultrasound probe configured to transmit ultrasound signals to a fetus and receive ultrasound echo signals reflected from the fetus;
a user inputter comprising a keyboard or a peripheral that is configured to receive, from a user, pregnancy information regarding a patient;
a communicator;
a controller configured to:
control the communicator to transmit, to a cloud server prestoring and accumulating fetal biometric data, a request signal requesting transmission of the fetal biometric data related to the received pregnancy information regarding the patient,
control the communicator to receive the fetal biometric data,
generate an ultrasound image of the fetus by using the ultrasound echo signals,
measure a size of a body part of the fetus on the ultrasound image,
predict the fetal growth rate based on the measured size of the body part of the fetus and the fetal biometric data received from the cloud server, and
control the communicator to receive a first data included in the fetal biometric data, the first data being related to the pregnancy information regarding the patient and to receive a second data included in the fetal biometric data, and the second data being related to characteristic information of the patient from among first big data with respect to a fetal biometric value,
wherein the characteristic information is stored in the cloud server, and
wherein the characteristic information comprises at least one of a location, an age, or physical characteristics of the patient; and
a display displaying a graph with a gestational week of the patient as a first axis and the fetal biometric data received from the cloud server as a second axis, a first user interface including a text indicating that the fetal biometric data is received from the cloud server and a second user interface indicating the pregnancy information,
wherein the graph, the first user interface, and the second user interface are displayed at the same time in different areas of a display,
wherein the communicator is further configured to receive, from the cloud server, second big data related to the fetal biometric data with respect to the gestational week, and
wherein the fetal biometric data is obtained by a plurality of different ultrasound imaging apparatuses and stored in the cloud server.

7. The ultrasound imaging apparatus of claim 6, wherein the controller is further configured to measure at least one of a biparietal diameter (BPD), an abdominal circumference (AC), a head circumference (HC), an occipitofrontal diameter (OFD), or a femur length (FL) of the fetus on the ultrasound image.

8. The ultrasound imaging apparatus of claim 6, wherein the user inputter is further configured to receive information about a last menstrual period (LMP) of the patient or a date of conception (DOC) of the fetus.

9. The ultrasound imaging apparatus of claim 6, wherein the controller is further configured to update a gestational age table and a fetal growth table by using the fetal biometric data received from the cloud server and predict the fetal growth rate based on a result of the updating and the measured size of the body part of the fetus.

10. The ultrasound imaging apparatus of claim 6, wherein the display displays on the graph a mark representing a value of the size of the body part of the fetus, wherein the size of the body part is measured with respect to the gestational week.

* * * * *